US009415000B2

(12) United States Patent
Washington et al.

(10) Patent No.: US 9,415,000 B2
(45) Date of Patent: Aug. 16, 2016

(54) HAIR STRAIGHTENING METHOD INVOLVING REDUCING SUGARS

(71) Applicant: The Procter & Gamble Company, Cincinnati, OH (US)

(72) Inventors: Randy Washington, West Chester, OH (US); Andreas Flohr, Kronberg (DE); Stephanie L. Davis, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/508,310

(22) Filed: Oct. 7, 2014

(65) Prior Publication Data

US 2015/0096584 A1   Apr. 9, 2015

(30) Foreign Application Priority Data

Oct. 7, 2013   (EP) .................................... 13187568

(51) Int. Cl.
| | |
|---|---|
| *A45D 7/06* | (2006.01) |
| *A61K 8/60* | (2006.01) |
| *A61Q 5/04* | (2006.01) |
| *A61K 8/81* | (2006.01) |
| *A61K 8/898* | (2006.01) |
| *A61K 8/19* | (2006.01) |
| *A45D 2/00* | (2006.01) |
| *A61K 8/25* | (2006.01) |

(52) U.S. Cl.
CPC . *A61K 8/60* (2013.01); *A45D 2/001* (2013.01); *A45D 7/06* (2013.01); *A61K 8/19* (2013.01); *A61K 8/25* (2013.01); *A61K 8/8182* (2013.01); *A61K 8/898* (2013.01); *A61Q 5/04* (2013.01); *A61K 2800/30* (2013.01); *A61K 2800/87* (2013.01); *A61K 2800/88* (2013.01)

(58) Field of Classification Search
None
See application file for complete search history.

(56) References Cited

U.S. PATENT DOCUMENTS

| | | | | |
|---|---|---|---|---|
| 4,364,837 | A | | 12/1982 | Pader |
| 4,690,818 | A | | 9/1987 | Puchalski |
| 5,110,318 | A | | 5/1992 | Altobelli |
| 5,641,477 | A | * | 6/1997 | Syed ........................ A61K 8/43 132/204 |
| 6,486,105 | B1 | * | 11/2002 | Cannell .................... A61K 8/60 510/119 |
| 7,815,900 | B1 | | 10/2010 | Cannell |
| 8,349,780 | B2 | | 1/2013 | Baker |
| 8,883,710 | B2 | | 11/2014 | Willey |
| 2002/0157682 | A1 | | 10/2002 | Ueyama |
| 2005/0048018 | A1 | | 3/2005 | Fadeeva |
| 2006/0257344 | A1 | | 11/2006 | Nguyen |
| 2007/0028938 | A1 | * | 2/2007 | Tiwari ...................... A61K 8/365 132/202 |
| 2009/0118421 | A1 | * | 5/2009 | Falk ........................ C07F 7/1836 524/588 |
| 2009/0283106 | A1 | | 11/2009 | Torgerson |
| 2009/0285768 | A1 | | 11/2009 | Baker |
| 2009/0320869 | A1 | | 12/2009 | Fadeeva |
| 2011/0256083 | A1 | | 10/2011 | Smith |
| 2012/0192887 | A1 | | 8/2012 | Vic |
| 2013/0319449 | A1 | | 12/2013 | Xavier |
| 2015/0173478 | A1 | | 6/2015 | Adams |
| 2015/0173479 | A1 | | 6/2015 | Adams |
| 2015/0173480 | A1 | | 6/2015 | Washington |
| 2015/0174023 | A1 | | 6/2015 | Washington |
| 2015/0174027 | A1 | | 6/2015 | Washington |
| 2015/0174028 | A1 | | 6/2015 | Washington |
| 2015/0174029 | A1 | | 6/2015 | Washington |
| 2015/0174030 | A1 | | 6/2015 | Washington |
| 2015/0174031 | A1 | | 6/2015 | Washington |
| 2015/0174032 | A1 | | 6/2015 | Washington |
| 2015/0174035 | A1 | | 6/2015 | Reed |
| 2015/0174036 | A1 | | 6/2015 | Washington |
| 2015/0174037 | A1 | | 6/2015 | Washington |
| 2015/0174432 | A1 | | 6/2015 | Adams |
| 2015/0174793 | A1 | | 6/2015 | Adams |
| 2015/0374604 | A1 | | 12/2015 | Kadir |

FOREIGN PATENT DOCUMENTS

| | | | |
|---|---|---|---|
| DE | 19812669 A1 | 10/1999 | |
| EP | 2111852 A2 | 10/2009 | |
| WO | WO02078655 A2 | 10/2002 | |
| WO | WO2009045556 | * 4/2009 | ............... A61K 8/65 |
| WO | WO2011074143 A1 | 6/2011 | |
| WO | WO2011089985 A1 | 7/2011 | |
| WO | WO2013098332 A2 | 7/2013 | |

OTHER PUBLICATIONS

Brazil Fabulous. https://web.archive.org/web/20100402084028/http://brazilianfab.wordpress.com/the-brazilian-keratin-clinic/your-keratin-questions-answered/. Published Apr. 2, 2010.*

Brazilian Keratin. http://www.verticalsinhair.com/index.php?option=com_content&view=category&layout=blog&id=43. Published 2010.*

(Continued)

*Primary Examiner* — David J Blanchard
*Assistant Examiner* — Lori K Mattison
(74) *Attorney, Agent, or Firm* — James T. Fondriest

(57) ABSTRACT

A hair straightening and/or hair relaxing method comprising: applying a hair care composition to hair, wherein the composition comprises a sugar, a buffering agent and a cosmetically acceptable carrier; and wherein, where the composition is heated to a temperature of at least 100° C., the composition comprises from about 6% to about 20% reducing sugar; hair drying; providing a hair straightening appliance at a temperature of from about 100° C. to about 280° C. and mechanically straightening the hair with the appliance.

7 Claims, No Drawings

(56) References Cited

OTHER PUBLICATIONS

Brazilian Blowout Zero. http://icanhasscience.com/chemistry/brazilian-blowouts-new-formula-sans-methylene-glycol/. Published Feb. 14, 2011.*
Whole World Botanicals. http://wholeworldbotanicals.com/camu-camu-myrciaria-dubia/. Published Mar. 1, 2003.*
Edible Medicinal and Non-Medicinal Plants. vol. 3. Lim. Copyright: 2012. p. 634.*
Bobbio. Cienc. Tecnol. Aliment. vol. 20, No. 3, Campas Sep.-Dec. 2003.*
Ajinomoto. http://www.ajichem.com/en/products/amino-acids.aspx. Published: Dec. 3, 2008.*
U.S. Appl. No. 14/972,926, filed Dec. 17, 2015, Washington.
U.S. Appl. No. 14/972,966, filed Dec. 17, 2015, Washington.
U.S. Appl. No. 14/972,993, filed Dec. 17, 2015, Washington.
U.S. Appl. No. 62/181,488, filed Jun. 18, 2015, Washington.
U.S. Appl. No. 62/181,499, filed Jun. 18, 2015, Washington.

* cited by examiner

HAIR STRAIGHTENING METHOD INVOLVING REDUCING SUGARS

FIELD OF THE INVENTION

A hair straightening and/or hair relaxing method comprising: applying a hair care composition to hair, wherein the composition comprises a sugar, a buffering agent and a cosmetically acceptable carrier; and wherein, where the composition is heated to a temperature of at least 100° C., the composition comprises from about 6% to about 20% reducing sugar; hair drying; providing a hair straightening appliance at a temperature of from about 100° C. to about 280° C. and mechanically straightening the hair with the appliance.

BACKGROUND OF THE INVENTION

Styling hair is about achieving a specific hairstyle e.g. achieving straight hair from curly hair. Hair may be styled using non-permanent and/or permanent methods. Consumers use a myriad of chemical treatments with and without external tools such as flat irons, blow dryers, etc to achieve and maintain a certain hairstyle.

Permanent methods—or relaxers—usually comprise the steps of applying onto hair a composition comprising a high pH solution (or combination of components to generate high pH), leaving on for a protracted time and then applying a neutralizing composition. A relaxer is a treatment predominately used by people of African-descent to permanently straighten hair. The treatment relies on either the one-step sodium hydroxide (lye) or a two step (e.g. guanidine carbonate and calcium hydroxide) to achieve very high pH (pH 12-14).

Semi-permanent benefits can be achieved using redox chemistry such as thioglycolic acid (TGA) and hydrogen peroxide. Here, the curly hair is transformed into the straight hair because the disulfide bonds are broken by the reaction with TGA. The straighter style is locked in during the oxidation step with hydrogen peroxide.

Non-permanent methods usually comprise the step of heating the hair with a flat-iron or heating element. Methods using such devices in combination with chemically-modifying the internal hair fibres can obtain long-lasting effects e.g. over several months. The Brazilian Keratin Treatments (BKTs) enable the achievement of a straight hairstyle that lasts several months via a shampoo treatment. The key active in BKTs is formaldehyde. The most efficacious treatments (used mainly in salons) rely on high temperature—usually 232° C. (450° F.)—with formaldehyde. Hair treated with products with high concentration of formaldehyde such as Brazilian Blowout delivers semi-permanent straight hair. Over time and following shampooing, the hair reverts back to a curly configuration.

The known methods for straightening hair all have drawbacks. The permanent methods are typically time-consuming and may damage hair. In addition, such methods show little flexibility so that any need and/or wish for changing the hairstyle would require conducting again a "permanent" wave onto hair, which is time-consuming and further damages the hair.

Along with the high potential skin irritation during application, relaxers tend to permanently change the hair by breaking the natural disulfide bonds in the hair. This leaves the hair weaker and more prone for further breakage. Over-processing can also increase hair damage and skin irritation. Consumer products using redox chemistry to achieve semi-permanent benefits, but over processing the hair and the strong sulphur smell are concerns of technologies based on reducing chemistry.

According to the US National Toxicology Program, formaldehyde is known to be a human carcinogen. Therefore, providing a semi-permanent style with carcinogen-free formulation is paramount. Given the safety concern of formaldehyde and the damaging effect of relaxers and reducing chemistry, there is a need for a safe alternative to durable straightening that does not break disulfide bonds.

None of the above methods allow achieving a hairstyle that may be retained and/or recovered after at least one shampoo treatment without severely damaging the hair or using a carcinogen active. There is a need for the provision of a method for achieving a hairstyle that lasts at least five shampoo treatments so that the user would not need to re-shape hair after each shampoo but would still have the opportunity to change hairstyle after some time and without needing to use stringent or harsh hair treatment, such as the permanent technologies outlined above.

WO2011/074143A1 (De Boni et al) discloses a process for treating keratin fibers comprising the steps of: applying onto the keratin fibers a composition comprising at least one saccharide or derivative thereof; then placing the keratin fibers in an occlusive space; and then heating the keratin fibers, wherein the composition contains neither a reducing agent nor a source of carbonate ions of the formula: wherein X is a group selected from the group consisting of O, OH, NH2, O—OH, and O—COO. However, WO2011/074143A1 requires the placing the placing the keratin fibers in an occlusive space. US2007/0226916A1 (Mellul et al) discloses a composition which, in a preferred embodiment, contains, in a cosmetically acceptable medium, at least one monosaccharide and/or disaccharide, at least one a-hydroxy acid, and at least one ceramide compound. Uses include topical application for the treatment of keratinous substances, in particular keratinous fibres, especially the hair. However, US2007/0226916A1 does not disclose hair straightening.

There is a need therefore for providing a method for achieving and semi-permanently retaining and/or recovering hairstyle using actives that do not break disulfide bonds (reducing agents) or that are considered carcinogenic. There is also the need for providing a method for obtaining a hairstyle exhibiting resistance to shampoo treatments. Particularly, there is a need for providing a method for retaining and/or recovering hairstyle after at least one shampoo treatment, particularly after five shampoo treatments, more particularly after ten shampoo treatments. In addition, there is a need for providing a method for achieving and retaining and/or recovering hairstyle, without damaging hair. Also, there is a need for providing more economic semi-permanent hair straightening or hair relaxing treatments. Moreover, there is a need for providing a hair straightening or hair relaxing treatment that does not employ an occlusive space such as via wrapping or covering the hair in a film or plastic sheet.

SUMMARY OF THE INVENTION

According to a first aspect, the present invention relates to a hair straightening and/or hair relaxing method comprising:
 (a) applying a hair care composition to hair, wherein the composition comprises a sugar, a buffering agent and a cosmetically acceptable carrier; and wherein, where the composition is heated to a temperature of at least 100° C., the composition comprises from about 6% to about 20% reducing sugar;
 (b) hair drying;

(c) providing a hair straightening appliance at a temperature of from about 100° C. to about 280° C. and mechanically straightening the hair with the appliance;

wherein the composition is substantially free of: formaldehyde, derivatives of formaldehyde, methylene glycol, formalin, and any compound that produces formaldehyde upon heating;

and wherein the composition has a pH of from about pH 6 to about pH 10;

wherein the method does not comprise a rinsing step between step (a) and step (c);

and wherein the method does not use any coating material.

According to a second aspect, the present invention relates to a hair straightening and/or hair relaxing regimen comprising the method according to the first aspect, wherein the complete method (a) to (c) is repeated at least 3 times at a frequency of at least once every 48 hours.

According to a third aspect, the present invention relates to a formulation for straightening hair comprising:

from about 12% to about 18% reducing sugar, wherein the reducing sugar is selected from the group consisting of: arabinose, ribose, and mixtures thereof;

a buffering agent;

a cosmetically acceptable carrier;

a conditioning agent being the reaction product of: (a) an aminosilane; (b); polysiloxane; and optionally (c) a polyether;

and wherein the composition has a pH of from about pH 6 to about pH 10.

According to a fourth aspect, the present invention relates to a kit for straightening hair comprising: (i) a formulation according to the third aspect; (ii) a heating device comprising a flat iron.

According to a fifth aspect, the present invention relates to the use of the formulation according to the third aspect for straightening hair.

DETAILED DESCRIPTION OF THE INVENTION

Definitions and General

In this document, including in all embodiments of all aspects of the present invention, the following definitions apply unless specifically stated otherwise. All percentages are by weight of the total composition. All ratios are weight ratios. References to 'parts' e.g. a mixture of 1 part X and 3 parts Y, is a ratio by weight. "QS" or "QSP" means sufficient quantity for 100% or for 100 g. +/− indicates the standard deviation. All ranges are inclusive and combinable. The number of significant digits conveys neither a limitation on the indicated amounts nor on the accuracy of the measurements. All numerical amounts are understood to be modified by the word "about". All measurements are understood to be made at 23° C. and at ambient conditions, where "ambient conditions" means at 1 atmosphere (atm) of pressure and at 50% relative humidity. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International. Herein "min" means "minute" or "minutes". Herein "mol" means mole. Herein "g" following a number means "gram" or "grams". All weights as they pertain to listed ingredients are based on the active level and do not include carriers or by-products that may be included in commercially available materials. Herein, "comprising" means that other steps and other ingredients can be in addition.

"Comprising" encompasses the terms "consisting of" and "consisting essentially of". The compositions, formulations, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated. "In an embodiment" means that one or more embodiments of the present invention has/have the subsequently described feature.

"Molecular weight" or "M. Wt." or "MW" and grammatical equivalents mean the number average molecular weight.

"Viscosity" is measured at 25° C. using a HAAKE Rotation Viscometer VT 550 with cooling/heating vessel and sensor systems according to DIN 53019 at a shear rate of $12.9\ s^{-1}$.

"Water-soluble" refers to any material that is sufficiently soluble in water to form a clear solution to the naked eye at a concentration of 0.1% by weight of the material in water at 25° C. The term "water-insoluble" refers to any material that is not "water-soluble".

"Dry" or "substantially dry" means comprising less than 5%, less than 3% or, less than 2%, less than 1%, or about 0% of any compound or composition being in liquid form when measured at 25° C. at ambient conditions. Such compounds or compositions being in liquid form include water, oils, organic solvents and other wetting agents. "Anhydrous" means that the composition comprises less than 5%, less than 3% or, less than 2%, less than 1%, or about 0% water by total weight of the composition.

"Substantially free from" or "substantially free of" means less than about 1%, or less than 0.8%, or less than 0.5%, or less than 0.3%, or about 0%, by total weight of the composition or formulation.

"Hair" means mammalian keratin fibres including scalp hair, facial hair and body hair. It includes such hair still being attached to a living subject and also hair that has been removed there from such as hair swatches and hair on a doll/mannequin. In an embodiment, "hair" means human hair. "Hair shaft" or "hair fibre" means an individual hair strand and may be used interchangeably with the term "hair."

"Proximal to the scalp" means that portion of an extended, or substantially straightened, hair shaft that is closer in distance to the scalp than to the end of the hair. Thus, about 50% of the hair fibre length would be considered proximal to the scalp, and about 50% of the hair fibre would be distal to the scalp. "z cm proximal to the scalp" means a distance "z" along the hair, with one endpoint being on or directly adjacent to the scalp, and the second endpoint being measured "z" centimeters along the length of the extended or substantially straightened hair.

"Chemically modify" or grammatical equivalents thereof, means that a chemical moiety such as monomer and/or crosslinker and/or polymer, stably affixes to a second chemical moiety, for example, a keratin protein, another component of hair, and/or another monomer or crosslinker or polymer. Normally, "chemically modify" means stably affix via a covalent bond, unless otherwise stated.

"Cosmetically acceptable" means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

"Derivatives" includes but is not limited to, amide, ether, ester, amino, carboxyl, acetyl, acid, salt and/or alcohol derivatives of a given compound. In an embodiment, "derivatives thereof" means the amide, ether, ester, amino, carboxyl, acetyl, acid, salt and alcohol derivatives.

"Monomer" means a discrete, non-polymerised chemical moiety capable of undergoing polymerisation in the presence of an initiator or any suitable reaction that creates a macromolecule e.g. such as polycondensation, polyaddition, anionic or cationic polymerization. "Unit" means a monomer that has already been polymerised i.e. is part of a polymer.

"Polymer" means a chemical formed from the polymerisation of two or more monomers. The term "polymer" shall include all materials made by the polymerisation of monomers as well as natural polymers. Polymers made from only one type of monomer are called homopolymers. Herein, a polymer comprises at least two monomers. Polymers made from two or more different types of monomers are called copolymers. The distribution of the different monomers can be random, alternating or block-wise (i.e. block copolymer). The term "polymer" used herein includes any type of polymer including homopolymers and copolymers.

"Hairstyling polymer" means a hair-fixing polymer which forms a film on a surface i.e. a film-forming polymer. 'Hairstyling polymer' and 'film-forming polymer' are used interchangeably in the art. In the context of hair science, this surface is the surface of individual hair fibres or a plurality thereof. The hairstyling polymer causes the hair fibres to be glued together to build welds, which are effectively crosslinks that provide the hold benefit. In concert, these welds form a 'hairnet' to provide hair hold and volume benefits to the consumer. When the net of welds is effectively formed, the hold and volume benefits can last all day and offer good resistance to environmental humidity.

"Kit" means a package comprising a plurality of components. "Kit" may be referred to as "kit-of-parts". An example of a kit is, for example, a first composition and a separately packaged second composition and optionally application instructions.

Advantages of the Invention

The present invention relates to hair straightening and/or hair relaxing method and is, in particular, a method for achieving a semi-permanent hairstyle. The present method comprising treating hair with a reducing sugar, followed by mechanically shaping i.e. straightening, allows achieving a semi-permanent hairstyle i.e. a durable hairstyle. This semi-permanent hairstyle is retained after at least one shampoo treatment, particularly after five shampoo treatments, more particularly after 10 shampoo treatments. Besides the increased durability of the hairstyle, this method prevents clumping of hair and/or improves post-shampoo detangling of hair and feel. In addition, the inventors have found that this method increases the water- and humidity-resistance of the hairstyle, increases the ease of style and/or increases the manageability of the hairstyle after shampoo. Without wishing to be bound by any theory, it is believed that the above benefits are due to the steps conducted, their sequence, as well as the specific components used including the reducing sugar. Another benefit of the invention is being able to achieve the semi-permanent benefits with natural or naturally-derived actives such as reducing sugars compared to non-natural actives. Particularly, the sugars are chosen so that sugars that show a positive Benedict's test under the conditions used.

Without wishing to be bound by any theory, it is believed that the selected reducing sugar diffuses into the hair and crosslinks the hair providing sufficient crosslinks to overcome the innate restoring force of the hair structure. This results in a durable hairstyle.

The present invention relates to a hair straightening and/or hair relaxing method. The method comprises applying a hair care composition to hair. For brevity, "hair care composition" is used interchangeably with "composition" hereinafter.

Composition

The method comprises (a) applying a hair care composition to hair, wherein the composition comprises a sugar, a buffering agent and a cosmetically acceptable carrier; and wherein, where the composition is heated to a temperature of at least 100° C., the composition comprises from about 6% to about 20% reducing sugar. What is meant by "where the composition is heated to a temperature of at least 100° C., the composition comprises from about X % to about Y % reducing sugar" is that if the composition was heated to a temperature of at least 100° C., the composition would thereafter comprise reducing sugar within the prescribed percentage range. This is in view of the heat energy causing chemical change in the sugar (e.g. degradation) that results in the formation of reducing sugar in the composition. This is in view of the method comprising "providing a hair straightening appliance at a temperature of from about 100° C. to about 280° C. and mechanically straightening the hair with the appliance" which would cause the chemical change in the sugar (e.g. degradation) that results in the formation of reducing sugar in the composition. Thus, whilst the presence of reducing sugar is important for the invention, it is sufficient to provide a composition comprising a certain non-reducing sugar, a buffering agent and a cosmetically acceptable carrier and then "providing a hair straightening appliance at a temperature of from about 100° C. to about 280° C. and mechanically straightening the hair with the appliance" which as a result of the heat, means that the non-reducing sugar is converted to reducing sugar. In an embodiment, the "heated to a temperature of at least 100° C." is carried out for from 2 sec to 10 min, or from 1 min to 5 min, or from 2 min to 3 min. In an embodiment, the composition comprises a reducing sugar and wherein, where the composition is heated to a temperature of at least 100° C., the composition comprises from about 12% to about 18% reducing sugar. In an embodiment, the composition comprises sucrose, a buffering agent and a cosmetically acceptable carrier; and wherein, where the composition is heated to a temperature of at least 100° C., the composition comprises from about 6% to about 20% reducing sugar. Sucrose is able to break down into reducing sugar following heating. In an embodiment, the sugar is a glucoside. In an embodiment, the sugar is methyl glucoside. In an embodiment, the sugar is a disaccharide. In an embodiment, the sugar is sucrose.

In an embodiment, the composition comprises a reducing sugar. In an embodiment, the composition comprises from about 7% to about 20%, or from about 8% to about 19%, or from about 10% to about 18% reducing sugar. In an embodiment, the composition comprises from about 12% to about 18% reducing sugar. In an embodiment, the composition comprises a reducing sugar and wherein, where the composition is heated to a temperature of 100° C., the composition comprises from about 12% to about 18% reducing sugar. In an embodiment, the composition comprises a total amount of reducing sugar being from about 12% to about 18% reducing sugar. In an embodiment, the reducing sugar has a M. Wt. of 500 g/mol or less, or from about 50 g/mol to about 300 g/mol. This is in view of penetration into hair.

In an embodiment, the composition comprises a reducing sugar and a cosmetically acceptable carrier. As used herein, "reducing sugar" means any sugar that either has an aldehyde group or is capable of forming an aldehyde group in solution through isomerism, and that gives a positive result in the Benedict's test. An aldehyde group is —C(=O)H. The aldehyde group is important in view of reacting with and crosslinking the hair. The Benedict's test involves employment of the Benedict's solution. The Benedict's solution is available from Sigma Aldrich as 'Benedict's Reagent', which comprises sodium carbonate, copper sulphate pentahydrate and 2,5-difluorotoluene. In the Benedict's test, 1 mL of Benedict's solution is added to a 20 mL of 5% aqueous solution comprising a dissolved test compound. Benedict's solution contains blue copper(II) ions ($Cu^{2+}$). The solution is heated to 80° C. for 15 min and the resulting colour change is noted. The cupric ion of the Benedict's solution is reduced to cuprous ion by the aldehyde of the sugar. A positive Benedict's test result is confirmed with a change in colour as cupric ions ($Cu^{2+}$) are converted to cuprous ions i.e. reduced to copper(I) ions ($Cu^+$). These are precipitated as red copper(I) oxide which is insoluble in water. The test is also designed for longer heating time and higher temperature to note any colour change. The solution may range in colour (with increasing amounts of reducing sugar) from green, through yellow and orange, to red. Any colour change away from blue suggest levels of reducing sugar. The wavelength of light reflected by the solution will change with the colour. In an embodiment, a positive Benedict's test result is when the solution emits light not peaking with a wavelength in the range of 450 nm to 495 nm. In an embodiment, a positive Benedict's test result is when the solution emits light peaking with a wavelength in the range of 620 nm to 750 nm. This can be measured using a spectrophotometer.

TABLE 1

Assessment of sugars using the Benedict's Test

| Sugar | 80° C., 15 min | 100° C., 40 min |
|---|---|---|
| Control solution* | Negative | Negative |
| Ribose | Positive | Positive |
| Arabinose | Positive | Positive |
| Glucose | Positive | Positive |
| Fructose | Positive | Positive |
| Xylose | Positive | Positive |
| Sucrose | Negative | Positive |
| Methyl glucoside | Negative | Positive |

*Benedict's solution only.

In the art, the Benedict's reagent is used as a test for the presence of reducing sugars. This includes all monosaccharides and many disaccharides, including lactose and maltose. Even more generally, Benedict's test will detect the presence of aldehydes, and alpha-hydroxy-ketones, including those that occur in certain ketoses. Thus, although fructose, a ketose, is not strictly a reducing sugar, it is an alpha-hydroxy-ketone, it gives a positive test because it is converted to the aldoses glucose and mannose by the base in the reagent. The copper sulphate in Benedict's solution reacts with reducing sugars. One liter of Benedict's reagent can be prepared from 100 g of anhydrous sodium carbonate, 173 g of sodium citrate and 17.3 g of copper(II) sulfate pentahydrate. Benedict's Reagent provides a quantitative test for reducing sugars along with qualitative test. The colour of the obtained precipitate gives an idea about the quantity of sugar present in the solution. A greenish precipitate indicates about 0.5% concentration; yellow precipitate indicates 1% concentration; orange indicates 1.5% and red indicates 2% or higher concentration. A positive result in the Benedict's test can be recognised for a compound by a 5% (weight/weight) solution of compound in water as a red colouring. The aldehyde group of the sugar allows the sugar to act as a reducing agent, for example in the Benedict's test.

In an embodiment, the reducing sugar is selected from the group consisting of: ribose, arabinose, xylose, lyxose, galactose, mannose, and mixtures thereof. In an embodiment, the reducing sugar is fructose or glucose. Sugars and reducing sugars are available from Sigma Aldrich. In an embodiment, the reducing sugar is either ribose, arabinose, or a mixture thereof. In an embodiment, the composition comprises a reducing sugar and wherein the reducing sugar is selected from the group consisting of: arabinose, ribose, and mixtures thereof. In an embodiment, the composition comprises a reducing sugar and wherein the reducing sugar is selected from the group consisting of: D-arabinose, L-arabinose, and mixtures thereof. In an embodiment, the reducing sugar is L-arabinose. In an embodiment, the sole reducing sugar is a pentose. In an embodiment, the sole reducing sugar is selected from the group consisting of: arabinose, ribose, and mixtures thereof. The reducing sugars arabinose, ribose, and mixtures thereof have the benefit of excellent straightening performance. By treating hair with reducing sugar and subsequent heat treatment as per the invention the treated hair becomes durably straight. Arabinose and ribose are 5 carbon sugars and these are found to have even better performance than sugars with other carbon numbers, such as 6 carbon and 7 carbon sugars. On the other hand, 6 carbon sugars are highly available and thus have economic advantages. In an embodiment, the composition comprises a total amount of reducing sugar being from about 12% to about 18% reducing sugar, and wherein the composition comprises arabinose.

In an embodiment, the composition comprises an antioxidant. An antioxidant is useful in view of providing longer-term stability for the composition. In an embodiment, the composition comprises a safe and effective amount of an antioxidant. In an embodiment, the composition comprises from about 0.001% to about 5%, or from about 0.5% to about 1.0% antioxidant. In an embodiment, the antioxidant is selected from the group consisting of: ascorbic acid (vitamin C), ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, peroxides including hydrogen peroxide, perborate, thioglycolates, persulfate salts, 6-hydroxy-2,5,7,8-tetramethylchroman-2-carboxylic acid (commercially available under the tradename Trolox™), gallic acid and its alkyl esters, especially propyl gallate, uric acid and its salts and alkyl esters, sorbic acid and its salts, lipoic acid, amines (e.g., N,N-diethylhydroxylamine, aminoguanidine), sulfhydryl compounds (e.g., glutathione), dihydroxy fumaric acid and its salts, lycine pidolate, arginine pilolate, nordihydroguaiaretic acid, bioflavonoids, curcumin, lysine, 1-methionine, proline, superoxide dismutase, silymarin, tea extracts, grape skin and/or grape seed extracts, melanin, rosemary extracts, and mixtures thereof. In an embodiment, the antioxidant is tocopherol sorbate or an ester of tocopherol. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit Chatterjee. In an embodiment, the antioxidant is sodium benzoate. In an embodiment, the antioxidant is ascorbic acid. Ascorbic acid has the benefit of enhancing the oxidative stability of the formulation. In an embodiment, the composition comprises a safe and effective amount of ascorbic acid. In an embodiment, the composition comprises from about 0.001% to about 5%, or from about 0.5% to about 1.0% ascorbic acid.

In an embodiment, the composition comprises a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage, in order to decrease the local iron load, which generates, as indicated above, a pro-oxidant situation and pigmentation. A chelating agent is useful in view of providing longer-term stability for the composition. In an embodiment, the composition comprises a safe and effective amount of a chelator or chelating agent. In an embodiment, the composition comprises a chelating agent, and wherein the chelating agent is selected from the group consisting of: N-hydroxysuccinimide, EDTA, NTA, deferoxamine, hydroxamic acids and their salts, phytic acid, phytate, gluconic acid and its salts, transferrine, lactoferrin, and mixtures thereof. In an embodiment, the composition comprises a safe and effective amount of chelating agent. In an embodiment, the composition comprises from about 0.001% to about 10%, or from about 0.01% to about 5%, or from about 0.1% to about 5%, or from about 0.5% to about 1.0% chelating agent. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. In an embodiment, the chelating agent is selected from the group consisting of: N-hydroxysuccinimide deferoxamine, lactoferrin, hydroxamic acids, gluconic acid, phytic acid, derivatives thereof, and mixtures thereof.

The hair care composition comprises a cosmetically acceptable carrier. In an embodiment, the cosmetically acceptable carrier is any carrier suitable for formulating the reducing sugar into a composition being suitable for application onto hair. In an embodiment, the cosmetically acceptable carrier is selected from either an aqueous medium or an aqueous-alcoholic medium. In an embodiment, when the carrier is an aqueous-alcoholic carrier, this carrier comprises water and an alcohol. In an embodiment, the alcohol is selected from the group consisting of: ethanol, isopropanol, propanol, and mixtures thereof. In an embodiment, when the carrier is an aqueous carrier, this carrier consists essentially of water and is substantially free of alcohol. In an embodiment, the composition comprises a safe and effective amount of cosmetically acceptable carrier. In an embodiment, the hair care composition comprises from about 0.1% to about 99%, or from about 1% to about 98%, or from about 10% to about 97%, or from about 30% to about 95% water.

In an embodiment, the hair care composition is in a form suitable for application onto hair. In an embodiment, the composition is in the form of an emulsion, a solution, or a dispersion. In an embodiment, the composition comprises a surfactant. The surfactant can be useful in providing an emulsion. In an embodiment, when being in the form of an emulsion, said emulsion may be a water-in-oil emulsion, an oil-in-water emulsion, or a multiple emulsion. An emulsion has the benefit of providing an easy-to-apply composition for the consumer to apply to the hair and has aesthetic advantages. The hair care composition may be a leave-in composition or a rinse-off composition.

The hair care composition may be in a form selected from: a shampoo; a hair conditioning composition; a hairstyling composition; or combinations thereof. When being a hairstyling composition, said composition may be a gel composition; a spray gel composition, optionally dispensed using a mechanical spray device and/or at least one propellant; a non-aerosol hairspray, optionally dispensed using a suitable mechanically operated spraying device; a foamable composition, optionally dispensed using devices for foaming; hair wax composition; hair lotion composition; hair cream composition; or combinations thereof.

The hair care composition may further comprise at least one cosmetic hair treatment agent selected from hairstyling polymers, conditioning agents, hair cleansing agents, or mixtures thereof.

In an embodiment, the composition comprises a hairstyling polymer. In an embodiment, the hairstyling polymer is selected from the group consisting of: non-ionic hairstyling polymer, anionic hairstyling polymer, zwitterionic and/or amphoretic hairstyling polymer, cationic hair styling polymer, or mixtures thereof. Suitable hairstyling polymers may be found in the CTFA International Cosmetics Ingredient Dictionary and Handbook, "Hair Fixatives", $12^{th}$ edition (2008). Suitable hairstyling polymers are, for example, those materials disclosed from page 12, line 5 to page 19, line 1 of the European patent application 08151246.9 filed on 11 Feb. 2008, which is incorporated herein by reference.

In an embodiment, the composition comprises from about 0.01% to about 10% by weight, or from about 0.1% to about 8%, or from about 0.1% to about 5% hairstyling polymer.

In an embodiment, the composition comprises a non-ionic hairstyling polymer. In an embodiment, the non-ionic hairstyling polymer is a natural or synthetic polymer. In an embodiment, the non-ionic hair styling polymers is a polymer obtained from the polymerisation of at least one type of monomer selected from: vinylpyrrolidone; vinylcaprolactam; vinyl esters; vinyl alcohol; vinyl acetate; (meth)acrylamide, and/or its derivatives; (meth)acrylic acid, its salts, and/or its derivatives; propylene and/or ethylene glycol acid; crotonic acid; or mixtures thereof. For example, such polymers are available under the trade names Luviskol® or Luviset Clear®.

In an embodiment, the composition comprises an anionic hairstyling polymer. In an embodiment, the anionic hairstyling polymer is selected from the group consisting of: acrylic acid/alkyl acrylate/Nalkylacrylamide terpolymer; vinyl acetate/crotonic acid copolymer; C1-C5-alkyl acrylate/(meth)acrylic acid copolymer; sodium polystyrenesulfonate; vinyl acetate/crotonic acid/vinyl alkanoate copolymer; vinyl acetate/crotonic acid/vinyl neodecanoate copolymer; aminomethylpropanol acrylate copolymer; vinylpyrrolidone/(meth)acrylic copolymer; methyl vinyl ether/maleic monoalkyl esters copolymer; aminomethylpropanol salts of allyl methacrylate/(meth)acrylate copolymer; ethyl acrylate/methacrylic acid copolymer; vinyl acetate/mono-nbutyl maleate/isobornyl acrylate copolymer; octylacrylamid/(meth)acrylic acid copolymer; polyesters of diglycol, cyclohexanedimethanol, isophthalic acid and sulfoisophthalic acid; and mixtures thereof.

In an embodiment, the composition comprises a zwitterionic or amphoteric hairstyling polymer. In an embodiment, the zwitterionic or amphoteric hairstyling polymer is selected from the group consisting of: alkylacrylamide/alkylaminoalkyl methacrylate/(meth)acrylic acid copolymers; copolymers which are formed from at least one first monomer type which has quaternary amine groups, and at least one second monomer type which has acid groups; copolymers of fatty alcohol acrylates, of alkylamine oxide methacrylate and at least one monomer chosen from acrylic acid and methacrylic acid; methacryloylethylbetaine/methacrylic acid and/or esters copolymers; polyquaternium-47; polyquaternium-43; oligomers or polymers, preparable from quaternary croton betaines or quaternary croton betaine esters; or mixtures thereof.

In an embodiment, the composition comprises a cationic hairstyling polymer. In an embodiment, the cationic hairstyling polymer is selected from the group consisting of homopolymers or copolymers where a quaternary nitrogen groups are present either in the polymer chain or as substituent on one or more of the cationic monomers. The monomers containing ammonium groups may be copolymerized with non-cationic monomers. Suitable cationic monomers may be unsaturated, free-radically polymerizable compounds which carry at least one cationic group, in particular ammonium-substituted vinyl monomers, such as, for example, trialkylmethacryloxyalkylammonium, trialkylacryloxyalkylammonium, dialkyldiallylammonium and quaternary vinylammonium monomers with cyclic, cationic nitrogen-containing groups, such as pyridinium, imidazolium or quaternary pyrrolidones, e.g. alkylvinylimidazolium, alkylvinylpyridinium, or alkylvinylpyrrolidone salts. The alkyl groups of these monomers are preferably lower alkyl groups, such as, for example, C1 to C7-alkyl groups, particularly preferably C1 to C3-alkyl groups. Suitable non-cationic monomers may be selected from (meth)acrylamide, derivatives thereof; acrylate, its derivative thereof; vinylcaprolactone, vinylcaprolactam, vinylpyrrolidone, vinyl esters, vinyl alcohol, propylene glycol or ethylene glycol. For example, suitable cationic hairstyling polymers are available under the tradenames Gafquat 755 N; Gafquat 734; Gafquat HS 100; Luviquat HM 550; Merquat Plus 3300; Gaffix VC 713; Aquaflex SF 40.

In an embodiment, the composition comprises a cationic hairstyling polymer derived from a natural polymer. In an embodiment, the cationic hairstyling polymer derived from a natural polymer is derived from a natural polymer selected from the group consisting of: cationic derivatives polysaccharides such as cellulose, starch and/or guar; chitosan, its salts, and/or its derivatives; or mixtures thereof. In an embodiment, the cationic hairstyling polymers are selected from the group consisting of: polyquaternium-4; polyquaternium-10; polyquaternium-24; guar hydroxypropyltrimonium chloride; chitosonium pyrrolidonecarboxylate; and mixtures thereof.

In an embodiment, the composition comprises a conditioning agent, or a hair conditioning agent. The hair care composition may comprise any suitable and conventional hair conditioning agents. The term "hair conditioning agent" herein means any cosmetically acceptable compound having a cosmetic effect on hair, such as providing gloss to hair, making hair more manageable, improving hair touch, improving combability and/or giving hair more volume. Suitable hair conditioning agents may be found in the CTFA International Cosmetics Ingredient Dictionary and Handbook, "Hair conditioning agents", 12$^{th}$ edition (2008). In an embodiment, the hair conditioning agent is selected from the group consisting of: cationic surfactants, non-ionic surfactants, silicone compounds, organic oily conditioning agents, and mixtures thereof. Suitable hair conditioning agents are, for example, those materials disclosed from page 19, line 3 to page 27, line 33 of the European patent application 08151246.9 filed on 11 Feb. 2008, which is incorporated herein by reference.

In an embodiment, the conditioning agent is a cationic surfactant. In an embodiment, the cationic surfactant comprises amino or quaternary ammonium moieties. In an embodiment, the composition comprises from about 0.05% to about 3.5%, or from about 0.1% to about 3.0%, or from about 0.5% to about 2.5%, or from about 1.0% to about 2.0% cationic surfactant. In an embodiment, cationic surfactant is according to Formula II:

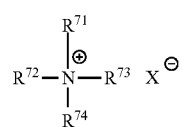

wherein at least one of $R^{71}$, $R^{72}$, $R^{73}$ and $R^{74}$ is selected from: an aliphatic group of from 8 to 30 carbon atoms; an aromatic, alkoxy, polyoxyalkylene, alkylamido, hydroxyalkyl, aryl; or an alkylaryl group having from 7 to 22 carbon atoms; wherein the remainder of $R^{71}$, $R^{72}$, $R^{73}$ and $R^{74}$ are independently selected from the group consisting of: an aliphatic group consisting of from 1 to 22 carbon atoms; and an aromatic, alkoxy, polyoxyalkylene, alkylamido, hydroxyalkyl, aryl or alkylaryl group having up to 22 carbon atoms; wherein X is selected from the group consisting of: halogen, acetate, citrate, lactate, glycolate, phosphate, nitrate, sulfonate, sulfate, alkylsulfate, alkyl sulfonate radicals, and mixtures thereof.

In an embodiment, cationic surfactant is according to Formula II (see above), wherein at least one of $R^{71}$, $R^{72}$, $R^{73}$ and $R^{74}$ is an aliphatic group having from 16 to 24 carbon atoms; wherein the remainder of $R^{71}$, $R^{72}$, $R^{73}$ and $R^{74}$ are independently selected from the group consisting of aliphatic groups having from 1 to 4 carbon atoms; wherein X is selected from the group consisting of: chloride or sulfate.

In an embodiment, the cationic surfactant is selected from the group consisting of: behenyltrimethylammonium chloride, methyl sulfate or ethyl sulfate; stearyltrimethylammonium chloride, methyl sulfate or ethyl sulfate; and mixtures thereof. It is believed that a longer alkyl group provides improved smoothness and soft feeling on wet and dry hair, compared to cationic surfactants with a shorter alkyl group. It is also believed that such cationic surfactants can provide reduced scalp irritation, compared to those having a shorter alkyl group.

In an embodiment, the cationic surfactant is a di-long alkyl quaternized ammonium salt selected from the group consisting of: dialkyl (14-18 carbons) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, and mixtures thereof.

In an embodiment, the cationic surfactant is a tertiary amidoamine having an alkyl group of from about 12 to about 22 carbons.

In an embodiment, the cationic surfactant is selected from the group consisting of: cetyl trimethyl ammonium salts; behenyl trimethyl ammonium salts; dimethyl ditallow ammonium salts; stearyl amidopropyl dimethylamine; (di)esterquats; quaternium 8, 14, 15, 18, 22, 24, 26, 27, 30, 33, 37, 53, 60, 61, 72, 78, 80, 81, 82, 83, 84, and/or 91; or mixtures thereof.

In an embodiment, the conditioning agent is a non-ionic surfactant. Suitable non-ionic surfactants may be surfactants having a HLB of less than 8. Suitable nonionic surfactants may be selected from glyceryl esters; sugar esters; alkylpolyglucoside ethers; oleyl- or isostearylpolyglucoside; polyoxyethylene (20) sorbitan monostearate; or mixtures thereof.

In an embodiment, the conditioning agent is a silicone compound. In an embodiment, the silicone compound is volatile or nonvolatile, and/or soluble or insoluble silicones. For example, suitable silicone conditioning agents are available under the tradenames SF 1075 methyl phenyl fluid (Electric company); DC200 Fluid, DC244, DC245, DC345, Dow 5-7113, DC556 Cosmetic Grade Fluid, DC1248 (Dow Corning). In an embodiment, the composition comprises a conditioning agent being the reaction product of: (a) an aminosilane; (b); polysiloxane; and optionally (c) a polyether. In an embodiment, the composition comprises a conditioning agent being the reaction product of: (a) an aminosilane; (b); polysiloxane; and (c) a polyether. In an embodiment, the composition comprises a conditioning agent, and wherein the conditioning agent is selected from the group consisting of: epoxyaminosilane copolymers, and polysiloxane/polyurea block copolymers, and mixtures thereof. In an embodiment, the composition comprises a conditioning agent being the reaction product of: (a) an aminosilane; (b) polysiloxane; and (c) a polyether; and optionally (d) an amine. In an embodiment, the polysiloxane is an epoxy encapped polysiloxane. In an embodiment, the polysiloxane comprises at least two oxirane or oxetane groups. In an embodiment, the polysiloxane comprises from about 10 to about 450 silicon atoms, or from about 40 to about 400 silicon atoms, from about 75 to about 350 silicon atoms, from about 150 to about 250 silicon atoms. In an embodiment, the polysiloxane is an epoxy encapped polysiloxane. In an embodiment, the polyether has the average structure $CH_2(O)CHCH_2O(CH_2(CH_3)CH_2O)_nCH_2CH(O)CH_2$ wherein n is an integer from 1 to 10. In an embodiment, the amine comprises from 1 to 10 carbon atoms, or from 2 to 5 carbon atoms. In an embodiment, the amine is an alkylamine that is substituted with at least one alkyl group. In an embodiment, the amine is selected from the group consisting of: methylamine, ethylamine, propylamine, ethanol amine, isopropylamine, butylamine, isobutylamine, hexylamine, dodecylamine, oleylamine, aniline aminopropyltrimethylsilane, aminopropyltriethylsilane, aminomorpholine, aminopropyldiethylamine benzylamine, napthylamine 3-amino-9-ethylcarbazole, 1-aminoheptaphlorohexane, 2,2,3,3,4,4,5,5,6,6,7,7,8,8,8-pentadecafluoro-1-octanamine, and mixtures thereof. In an embodiment, the amine is selected from the group consisting of: methylethylamine, methylhexylamine, methyloctadecylamine, diethanolamine, dibenzylamine, dihexylamine dicyclohexylamine, piperidine, pyrrolidine phthalimide, and mixtures thereof. In an embodiment, the conditioning agent is an epoxyaminosilane copolymer. In an embodiment, the conditioning agent is conditioning agent being the reaction product of: (a) an aminosilane; (b) polysiloxane, wherein the polysiloxane comprises from about 10 to about 450 silicon atoms, or from about 40 to about 400 silicon atoms; and (c) a polyether; and (d) an amine, wherein the amine is an alkylamine that is substituted with at least one alkyl group. Epoxyaminosilane copolymers are described in EP2214633B1 (filing date 30$^{th}$ Oct. 2008, which is incorporated herein by reference) and are available from Momentive™ Performance Materials Inc., Columbus, Ohio, USA. Epoxyaminosilane copolymers have excellent durability benefits. Such an exemplary expoxyaminosilane copolymer may be synthesised as follows: aminopropyltriisopropoxy silane (40.77 g), an epoxy encapped polysiloxane with the average structure $CH_2(O)CHCH_2OCH_2CH_2Si(CH_3)_2O[Si(CH_3)_2O]_{50}Si(CH_3)_2CH_2CH_2CH_2OCH_2CH(O)CH_2$ (171.40 g) and an epoxy endcapped polyether with the average structure $CH_2(O)CHCH_2O(CH_2(CH_3)CH_2O)_7CH_2CH(O)CH_2$ (37.83 g) and isopropanol (425.68 g) is combined in a 500 mL flask. The material is brought to reflux and stirred with an overhead stirrer. The refluxing continued for 15.5 hr until all epoxy groups are consumed as determined by titration. The material is transferred to a rotary evaporator and stripped at 70° C. and 532 Pa (4 torr) for 2 hrs to remove the isopropanol. Another exemplary expoxyaminosilane copolymer may be synthesised as follows: aminopropyltriisopropoxy silane (14.27 g), 3-(diethylamino)propylamine (7.05 g), an epoxy encapped polysiloxane with the average structure $CH_2(O)CHCH_2OCH_2CH_2Si(CH_3)_2O[Si(CH_3)_2O]_{200}Si(CH_3)_2CH_2CH_2CH_2OCH_2CH(O)CH_2$ (447.87 g) and an epoxy encapped polyether with the average structure $CH_2(O)CHCH_2O(CH_2CH_2O)_{14}CH_2CH(O)CH_2$ (30.81 g) and isopropanol (500 g) is combined in a 2000 mL flask. The material is brought to reflux and stirred with an overhead stirrer. The refluxing continued for 24 hr until all epoxy groups are consumed as determined by titration. The material is transferred to a rotary evaporator and stripped at 70° C. and 532 Pa (4 torr) for 2 hrs to remove the isopropanol.

In an embodiment, the conditioning agent is selected from the group consisting of: epoxyaminosilane copolymers, and polysiloxane/polyurea block copolymers, and mixtures thereof. A polysiloxane/polyurea block copolymer is described in EP2074986B1 filed on 10$^{th}$ Dec. 2008, which is incorporated herein by reference. In an embodiment, the polysiloxane/polyurea block copolymer comprises at least one polysiloxane sequence (or block) and at least one polyurea sequence (block) in the backbone of the copolymer. In an embodiment, the amount of polysiloxane present in the copolymer is greater than 90% by weight relative to the total weight of the polysiloxane/polyurea block copolymer. In at least one embodiment, the polysiloxane/polyurea block copolymer of the does not comprise polyurethane. By way of non-limiting example, the copolymer can be a non-ionic polysiloxane/polyurea copolymer, that is to say that it does not comprise an ionized or ionizable group. By way of example of a copolymer, non-limiting mention may be made of the dimethylpolysiloxane/polyurea block copolymer having the INCI name polyureadimethicone. Such a dimethylpolysiloxane/polyurea block copolymer can be obtained, for instance, by copolymerization of an α,ω-aminosilicone with a diisocyanate. Polysiloxane/polyurea block copolymers corresponding to these characteristics are, for example, the products sold under the reference Wacker-Belsil® UD 60, Wacker-Belsil® UD 80, Wacker-Belsil® DU 140 and Wacker-Belsil® UD 200 by Wacker. In an embodiment, the polysiloxane/polyurea copolymer is non-ionic. In an embodiment, the composition comprises from about 0.05 to about 20%, for example from 0.1 to 15%, or from 0.5 to 10% polysiloxane/polyurea block copolymer.

In an embodiment, the conditioning agent is an organic oily conditioning agent. In an embodiment, the organic oily conditioning agent is non-volatile, water-insoluble, oily or fatty. Organic oily conditioning agents may be selected from hydrocarbon oils and fatty esters.

In an embodiment, the conditioning agent is a fatty alcohol. In an embodiment, the fatty alcohol is a non-volatile low melting point fatty alcohol. In an embodiment, the conditioning agent is a fatty alcohol and the fatty alcohol is selected from the group consisting of: capryl alcohol, lauryl alcohol, stearyl alcohol, cetyl alcohol, myristyl alcohol, palmitoleyl alcohol, and mixtures thereof.

The composition may further comprise at least one direct hair dye. In an embodiment, the composition comprises from about 0.01% to about 15%, or from about 0.1% to about 10%, or from about 0.5% to about 8% direct hair dye.

The composition may further comprise at least one viscosity-modifying substance. In an embodiment, the composition comprises from about 0.01% to about 20%, or from about 0.05% to about 10%, or from about 0.1% to about 5% viscosity-modifying substance.

The hair care composition may further comprise at least one emulsifier and/or surfactant not being a hair conditioning agent. In an embodiment, the emulsifier and/or surfactant is selected from nonionic surfactants; anionic surfactants; amphoretic surfactants; or mixtures thereof. In an embodiment, the composition comprises from about 0.01% to about 20%, or from about 0.05% to about 10%, or from about 0.1% to about 5%, emulsifier and/or surfactant.

The hair care composition may further comprise at least one pigment. In an embodiment, the pigment is selected from natural pigments; synthetic pigments; or mixtures thereof. The pigments may be selected from organic pigment, inorganic pigment; or mixtures thereof. The pigments may be selected from coloured pigments; pearlescent pigments; or mixtures thereof. Said composition may comprise from about 0.01% to 10%, or from about 1% to about 2% pigment present in the product mass in undissolved form by weight of the total composition. The composition may comprise pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water-soluble components such as those having C.I. Names.

In an embodiment, the hair care composition comprises at least one particulate substance. In an embodiment, the particulate substance is selected from silica; silicates; aluminates; clay earths; mica; insoluble salts, particularly insoluble inorganic metal salts; metal oxides; minerals; insoluble polymer particles; or mixtures thereof. In an embodiment, the composition comprises from about 0.01% to about 10%, or from about 0.05% to about 5% of at least one particulate substance. In an embodiment, the composition is substantially free of a particulate substance such as clay.

In an embodiment, the composition comprises at least one photoprotective substance. In an embodiment, the composition comprises from about 0.01% to about 10%, or from about 0.1% to about 5%, or from about 0.2% to about 2% photoprotective substance. Photoprotective substances are useful in protecting the hair and composition from sunlight.

In an embodiment, the composition comprises at least one preservative. In an embodiment, the composition may comprise from about 0.01% to about 5% by weight, or from about 0.05% to about 1% preservative.

A variety of additional optional ingredients may be incorporated into the composition of the present invention. Non-limiting examples of these additional ingredients may be selected from preservatives; antioxidants; sequestering agents; solvents; fragrances & perfumes; fillers; screening agents; odour absorbers; colouring materials; lipid vesicles; detersive surfactants; thickening agents and suspending agents; viscosity modifiers; pearlescent aids; UV-filters and sunscreens; agents for combating free radicals; polyvinyl alcohol; pH adjusting agents; salts; colouring agents; polymer plasticizing agents; direct dyes; or mixtures thereof. The composition may comprise from about 0%, or from about 0.1% to about 5% antimicrobial agents. In an embodiment, the composition comprises an organic acid selected from the group consisting of: glycine, L-methionine, L-arginine, biotin, creatine, and mixtures thereof. In an embodiment, the composition comprises an antidandruff agent. In an embodiment, the composition comprises zinc pyrithione. In an embodiment, the composition comprises panthenol. In an embodiment, the composition comprises a wax compound. In an embodiment, the composition comprises beeswax.

In an embodiment, the hair care composition has a viscosity, measured at 25° C., of from about 0.1 mPa·s to about 1,000,000 mPas, or from about 1 mPa·s to about 80,000 mPa·s, or from about 5 mPa·s to about 3,500 mPa·s. The viscosity is measured by HAAKE Rotation Viscometer VT 550 with cooling/heating vessel and sensor systems according to DIN 53019 (MV-DIN, SV-DIN), shear rate is 12.9 s$^{-1}$.

The composition is substantially free of: formaldehyde, derivatives of formaldehyde, methylene glycol, formalin, and any compound that produces formaldehyde upon heating. "Heating" means raising the temperature of the compound above 25° C. In an embodiment, the composition comprises 0% formaldehyde. In an embodiment, the derivatives of formaldehyde are 1,3,5-trioxane and paraformaldehyde. In an embodiment, the composition is substantially free of: formaldehyde, 1,3,5-trioxane, paraformaldehyde, methylene glycol, formalin. Formaldehyde is not preferred in view of its safety profile. Formalin is not advantageous because formalin is a derivative of formaldehyde. Formaldehyde exists in multiple forms. In water, formaldehyde becomes hydrated and forms methylene glycol. A saturated solution of formaldehyde (about 40% formaldehyde) in water is more commonly known as formalin. Methanol and/or methylene diol can be used as a stabilizer in formalin and is therefore not advantageous. In an embodiment, the composition is substantially free of a quaternary ammonium compound and/or a surfactant. In an embodiment, the composition is substantially free of: ceramide compound, an alpha-hydroxy acid, a thioglycolate and/or thiolactate compound, a bisulfate compound, clay, a reducing agent. In an embodiment, the composition is substantially free of: ceramide compound, an alpha-hydroxy acid, a thioglycolate and/or thiolactate compound, a bisulfate compound. In an embodiment, the composition is substantially free of: carbonate compound. In an embodiment, the composition is substantially free of: ceramide compound, an alpha-hydroxy acid, a thioglycolate or thiolactate compound, a bisulfate compound, clay, formaldehyde, 1,3,5-trioxane, paraformaldehyde, methylene glycol, quaternary ammonium compound, surfactant.

The composition has a pH of from about pH 6 to about pH 10. In an embodiment, the composition has a pH of from about pH 6.5 to about pH 9.75, or from about pH 7.0 to about pH 9.5, or from about pH 7.5 to about pH 9.25, or from about pH 8.0 to about pH 9.0. The hair care composition comprises a buffering agent. In an embodiment, the buffering agent is a phosphate buffer. In an embodiment, the buffering agent is a borate buffer or a carbonate buffer. In an embodiment, the buffering agent is selected from the group consisting of: glycine/sodium hydroxide; sodium carbonate/sodium hydrogen carbonate, sodium tetraborate/sodium hydroxide; sodium bicarbonate/sodium hydroxide; ammonium chloride/ammonia. The buffering agent has the advantage of controlling the pH, which aids the stability of the composition.

In an embodiment, the composition comprises an alkalizing agent and/or an agent for adjusting the pH value. The composition may further comprise a protonating agent. The protonating agent may be a monoprotic or polyprotic acid, water-soluble or water-insoluble acid, and/or an organic or inorganic acid. In an embodiment, the protonating agent is selected from formic acid, acetic acid, sulfuric acid, hydrochloric acid, citric acid, and mixtures thereof. In an embodiment, the protonating agent is citric acid. Citric acid is useful because it is naturally available from lemons.

Method

The present invention relates to a hair straightening and/or hair relaxing method comprising: (a) applying a hair care composition to hair; (b) hair drying; (c) providing a hair straightening appliance at a temperature of from about 100° C. to about 280° C. and mechanically straightening the hair with the appliance; wherein the method does not comprise a rinsing step between step (a) and step (c); and wherein the method does not use coating material. The method steps are in the order (a) then (b) then (c). In the method of the present invention, the hair care composition may be applied on wet hair and/or on dry hair.

It is not preferred to employ a rinsing step between step (a) and step (c) because less straightening durability is observed. Indeed, it is believed that reduced penetration into the hair shaft exists when the sugar molecules are rinsed off prior to step (c).

The method does not use any coating material. In an embodiment, the method does not use any coating material selected from film coating material and sheet coating material. In an embodiment, the method does not use any coating means. Examples of film coating material or sheet coating material include plastic films, metal (foil) films. In an embodiment, method does not employ any: plastic film; foil; flexible heating film. Examples of such coating films and coating materials are disclosed in claim 1 and the examples of WO2011/074143A1, which published on 23rd Jun. 2011, and which is incorporated herein by reference. Indeed, such coating means is not preferred in view of the effect of such occlusive material in forming a condensation cage in which the cosmetically acceptable carrier a component or components in the composition may evaporate from the keratin fibers, adhere to the wall of the coating means, and drop onto the keratin fibers". In an embodiment, the method does not employ placing the keratin fibers in an occlusive space. "Film coating material" and "coating means" does not include liquid coating materials/means that then dry onto the hair. Examples of such liquid coating materials/means includes hairstyling polymers which are sometimes referred to as film-forming polymers.

In an embodiment, prior to step (a) the hair is washed with a shampoo, for example a cleansing shampoo. In an embodiment, following step (c) the hair is washed with a shampoo, for example a cleansing shampoo. In an embodiment, following step (c) the hair is washed with a shampoo, for example a cleansing shampoo, and subsequently conditioned with a conditioning formulation comprising a conditioning agent. Conditioning agents are disclosed herein and are suitable for this embodiment. In an embodiment, following step (c) the hair is washed with a shampoo and then conditioned with a conditioning formulation comprising a conditioning agent and then dried using a blow dryer and a brush. In an embodiment, the method comprises, prior to step a), providing hair that has already been straightened. Indeed, providing hair that has already been straightened has the advantage that the present treatment is relatively gentle and therefore highly suitable for hair that has been previously damaged by less gentle treatments. Consumers believe that where they have used e.g. a formaldehyde-based treatment previously, they cannot use another straightening treatment until the damage has grown out/been trimmed off. This is not the case for the present invention since it offers a semi-durable and gentle, yet efficacious straightening treatment that is highly suited to hair that has already been straightened.

In an embodiment, the method relates to a hair straightening and/or hair relaxing method comprising: (a) applying a hair care composition to hair, wherein the composition comprises from about 6% to about 20% reducing sugar, and wherein the reducing sugar is selected from the group consisting of: arabinose, ribose, and mixtures thereof; (b) hair drying; (c) providing a hair straightening appliance at a temperature of from about 100° C. to about 280° C. and mechanically straightening the hair with the appliance; wherein the composition is substantially free of: formaldehyde, derivatives of formaldehyde, methylene glycol, formalin, and any compound that produces formaldehyde upon heating; and wherein the composition has a pH of from about pH 6 to about pH 10; wherein the method does not comprise a rinsing step between step (a) and step (c); and wherein the method does not use any coating material; and optionally wherein the composition comprises a conditioning agent, and wherein the conditioning agent is an epoxyaminosilane copolymer.

Applying a Hair Care Composition to Hair

The present invention relates to a hair straightening and/or hair relaxing method comprising: (a) applying a hair care composition to hair. In an embodiment, applying a hair care composition to hair involves applying onto hair from about 0.01 gram to about 5 gram of said composition per gram hair. In an embodiment, the composition is on the hair for at least 2 min, or from about 5 min to about 45 min, or from about 10 min to about 40 min, or from about 20 min to about 35 min, prior to carrying out step b).

Hair Drying

The hair straightening and/or hair relaxing method comprises (b) hair drying. In an embodiment, the hair drying is carried out by a blow drier. In an embodiment, the hair drying is carried out for a duration of from about 1 min to about 45 min, or from about 2 min to 20 min, or from about 5 min to 15 min. In general, following the hair drying, the hair can still be damp, but needs to have reasonable e.g. 75% hair fibre separation of the head of hair. Some residual moisture in the hair is acceptable. In an embodiment, the hair is not wetted or rinsed prior to step (c). A high level of moisture is not preferred in view of hair damage caused by steam during step (c). Thus, the hair drying step (b) provides a method with reduced hair damage versus conventional methods.

In an embodiment, the hair drying is carried out by a hood appliance. In an embodiment, the hair drying is carried out by toweling hair and/or by pressing hair with hands.

Hair dryer or blow dryer distances between device and head are typically down to about 10 cm. Blow dryers direct hot air through some sort of attachment for combing or otherwise treating the hair. A blow dryer is typically used such that the distance to the hair (for example at a distance of 20 or 30 or 40 centimeters) and often is used with the aid of a comb or a brush. In an embodiment, the hair drying is carried out by a blow drier at a temperature of from about from 50° C. to about 100° C. In an embodiment, the hair drying is carried out by a blow drier at a temperature of up to 130° C. In an embodiment, the hair drying (b) is carried out with a blow drier with brushing to help straightening the hair.

Providing a Hair Straightening Appliance and Mechanically Straightening the Hair The hair straightening and/or hair relaxing method comprises (c) providing a hair straightening appliance at a temperature of from about 100° C. to about 280° C. and mechanically straightening the hair with the appliance. In an embodiment, the temperature is from about 110° C. to about 250° C., or from about 120° C. to about 240° C., or from about 140° C. to about 230° C., or from about 160° C. to about 220° C., or from about 180° C. to about 210° C., or from about 190° C. to about 200° C.

In an embodiment, the hair straightening appliance comprises metal or ceramic plates. In an embodiment, the metal or ceramic plates are provided to a temperature of from about 100° C. to about 280° C. In an embodiment, the metal or ceramic plates are provided to a temperature of from about 110° C. to about 250° C., or from about 120° C. to about 240° C., or from about 140° C. to about 230° C., or from about 160° C. to about 220° C., or from about 180° C. to about 210° C., or from about 190° C. to about 200° C.

In an embodiment, the 'mechanically straightening the hair with the appliance' is carried out for a duration of from about 1 min to about 45 min, or from about 2 min to 20 min, or from about 5 min to 15 min. In an embodiment, the 'mechanically straightening the hair with the appliance' is carried out for a duration of for at least 10 min, or for at least 12 min.

In an embodiment, the 'mechanically straightening the hair with the appliance' is carried out by a hair straightening appliance. In an embodiment, the hair straightening appliance comprises metal or ceramic plates. In an embodiment, the hair straightening appliance is a pair of straightening irons. Hair straightening appliances comprising metal or ceramic plates, such straightening irons typically rely on resistive heating, but heat is not transported through hot air, but by direct contact of the plates with the keratin fibres. The direct contact is often made by bringing the hair in contact with some metal or ceramic surface of the appliance. These devices typically are not or at least not primarily used to dry the hair. Rather are they used to change the hair style, typically either to create curls or to straighten hair. The surfaces meant for hair contact (e.g. metal or ceramic plates) of these devices typically reach temperatures from 130° C. to 250° C. Most devices have metal or ceramic plates used with temperatures from 160° C. to 230° C.

U.S. Pat. No. 5,612,849 and U.S. Pat. No. 6,191,930, which are incorporated herein by reference, disclose a heat generating hair care appliance in the form of a hot air hair care appliance. The respective devices are typically referred to as hair dryers or blow dryers. USD383245, which is incorporated herein by reference, discloses another heat generating hair care appliance in the form of a hot air hair care appliance. The respective devices are typically referred to as hot air stylers or hair stylers. US2008/0196739, which is incorporated herein by reference, discloses a heat generating hair care appliance in the form of a hot surface hair care appliance, typically referred to as a straightening irons.

$2^{nd}$ Aspect

According to the second aspect, the present invention relates to a hair straightening and/or hair relaxing regimen comprising the method according to any of the preceding claims, wherein the complete method (a) to (c) is repeated at least 3 times at a frequency of at least once every 48 hours. All the description in relation to the other aspects is suitable for and combinable with this aspect as well. In an embodiment, the complete method (a) to (c) is repeated at least 2 times at a frequency of at least once every 24 hours. In an embodiment, the complete method (a) to (c) is repeated at least 5 times at a frequency of at least once every 48 hours, or once every 24 hours.

$3^{rd}$ Aspect

According to the third aspect, the present invention relates a formulation for straightening hair comprising:
  from about 12% to about 18% reducing sugar, wherein the reducing sugar is selected from the group consisting of: arabinose, ribose, and mixtures thereof;
  a buffering agent;
  a cosmetically acceptable carrier;
  a conditioning agent being the reaction product of: (a) an aminosilane; (b); polysiloxane; and optionally (c) a polyether;

and wherein the composition has a pH of from about pH 6 to about pH 10.

All the description in relation to the other aspects is suitable for and combinable with this aspect as well. In an embodiment, the formulation is for curling and/or perming hair. In an embodiment, the formulation is for shaping hair. In an embodiment, the formulation comprises from about 0.1% to about 15%, or from about 1% to about 10%, or from about 2% to about 5% conditioning agent being the reaction product of: (a) an aminosilane; (b); polysiloxane; and optionally (c) a polyether. In an embodiment, the conditioning agent is the reaction product of: (a) an aminosilane; (b); polysiloxane; (c) a polyether.

$4^{th}$ Aspect

According to the fourth aspect, the present invention relates a kit for straightening hair comprising: (i) a formulation according to the $3^{rd}$ aspect; (ii) a heating device comprising a flat iron. All the description in relation to the other aspects is suitable for and combinable with this aspect as well. In an embodiment, the kit is for perming and/or curling hair. In an embodiment, the kit is for semi-permanent shaping of hair.

$5^{th}$ Aspect

According to the fifth aspect, the present invention relates the use of a formulation according to the $3^{rd}$ aspect for straightening hair. All the description in relation to the other aspects is suitable for and combinable with this aspect as well. Alternatively, the use is of a formulation according to the $3^{rd}$ aspect for shaping hair. Alternatively, the use is of a formulation according to the $3^{rd}$ aspect for curling and/or perming hair.

Further Aspects

In another aspect, the present invention relates to a hair curling and/or perming method comprising:
  (a) applying a hair care composition to hair, wherein the composition comprises a sugar, a buffering agent and a cosmetically acceptable carrier; and wherein, where the composition is heated to a temperature of at least 100° C., the composition comprises from about 1% to about 20% reducing sugar;
  (b) hair drying;
  (c) providing a hair curling appliance at a temperature of from about 100° C. to about 280° C. and mechanically curling the hair with the appliance;
  wherein the composition is substantially free of: formaldehyde, derivatives of formaldehyde, methylene glycol, formalin, and any compound that produces formaldehyde upon heating;
  and wherein the composition has a pH of from about pH 6 to about pH 10;
  wherein the method does not comprise a rinsing step between step (a) and step (c);
  and wherein the method does not use any coating material.
In an embodiment, the composition comprises a reducing sugar and wherein the reducing sugar is selected from the group consisting of: arabinose, ribose, and mixtures thereof. All the description in relation to the other aspects is suitable for and combinable with this aspect as well.

In another aspect, the present invention relates to a hair straightening and/or relaxing method comprising: providing hair that has already been straightening; and then
  (a) applying a hair care composition to the hair, wherein the composition comprises a sugar, a buffering agent and a cosmetically acceptable carrier; and wherein, where the composition is heated to a temperature of at least 100° C., the composition comprises from about 1% to about 20% reducing sugar;

(b) hair drying;

(c) providing a hair curling appliance at a temperature of from about 100° C. to about 280° C. and mechanically curling the hair with the appliance;

wherein the composition is substantially free of: formaldehyde, derivatives of formaldehyde, methylene glycol, formalin, and any compound that produces formaldehyde upon heating;

and wherein the composition has a pH of from about pH 6 to about pH 10;

wherein the method does not comprise a rinsing step between step (a) and step (c);

and wherein the method does not use any coating material.

In an embodiment, the composition comprises a reducing sugar and wherein the reducing sugar is selected from the group consisting of: arabinose, ribose, and mixtures thereof. All the description in relation to the other aspects is suitable for and combinable with this aspect as well.

EXAMPLES

The following examples further describe and demonstrate embodiments within the scope of the present invention. The examples are given solely for the purpose of illustration, and are not to be construed as limitations of the present invention since many variations thereof are possible without departing from its scope. All weights provided in these examples are weights of the commercially available materials, including active(s) and/or solvent and/or by-products.

Example Compositions

Liquid A: 15 g arabinose, 2 g epoxyaminosilane copolymer, QSP water

Liquid B: 15 g arabinose, 1 g epoxyaminosilane copolymer, 0.1 g NaOH, QSP water.

Liquid C: 10 g arabinose, 2 g epoxyaminosilane copolymer, pH10 buffer (buffer is borate or carbonate), QSP water.

Liquid gel: 12.00 g arabinose; 1.00 g Luviset Clear, 1.50 g surfactant 193, 0.30 g Carbomer, 0.30 g aminomethylpropanol (aka AMP) 95%, 0.20 g Emulgin L, 0.15 g perfume, 0.40 g Natrosol G, 16.50 g ethanol, QSP water.

Rapid Drying Gel: 12.00 g arabinose, 1.00 g Luviset Clear, 1.80 g Polyvinylpyrrolidone K 90; 1.00 g direct dye; 1.50 g surfactant 193; 1.00 g Synthalen W 2000; 0.30 g AMP (95%); 0.30 g PEG-25 PABA (Uvinul P 25); 0.15 g Panthenol; 0.30 g perfume; 34.20 g ethanol; 0.10 g keratin hydrolysate; QSP water.

Pump, setting foam: 10.00 g arabinose, 1.80 g Luviset Clear, 1.90 g direct dye, 0.40 g Cocamidopropyl Hydroxysultaine, 0.10 g Rosemary leaf extract (Extrapon Rosemary), 8.90 g ethanol, 0.10 g Extrapon seven herbs—extract, 0.10 g Panthenyl ethyl ether, 0.15 g Perfume, QSP water. The composition is packaged in a packaging with mechanically operated pump foaming device.

Aerosol—setting foam—extra strong hold: 8.00 g arabinose, 2.10 g Luviset Clear, 0.60 g Vinyl acetate/crotonic acid copolymer, 0.50 g Polyquaternium-7, 4.00 g butane, 4.00 g propane, 8.90 g ethanol 510, 0.40 g PEG-25 PABA, 0.20 g Panthenol, 0.20 g perfume, 0.20 g Laureth-4, 0.07 g C9-C11 Pareth-8, QSP 100.00 g water. The composition is bottled in an aerosol can with foaming head.

Setting spray: 10.2 g ribose, 1.00 g Luviset Clear, 0.65 g Octylacrylamide/Acrylates/Butylaminoethylmethacrylate Copolymer (Amphomer), 0.20 g Celquat L200, 28.5 g ethanol, 0.60 g aminomethylpropanol 95%, 0.25 g perfume, 0.20 g Cetyltrimethylammonium chloride, QSP 60.00 g water. The composition is bottled in a packaging with pump spray device.

Rinse-out conditioner: 9.30 g xylose, 1.00 g cetyltrimethyl ammonium chloride, 1.00 g polymethylphenyl siloxane, 0.40 g phenoxy ethanol, 0.20 g PHB-methylester, 1.00 g Dow Corning 949 Cationic Emulsion®, 5.00 g isododecane, 0.40 g perfume oil, QSP water.

Rinse-out Conditioner: 9.30 g arabinose, 1.00 g cetyltrimethyl ammonium chloride, 1.00 g polymethylphenyl siloxane, 0.40 g phenoxyethanol, 0.20 g PHB-methylester, 8.00 g Dow Corning 57113 Cationic Emulsion®, 5.00 g isododecane, 0.40 g perfume oil, QSP water.

Leave-in Conditioner: 9.30 g arabinose, 1.00 g cetyltrimethyl ammonium chloride, 1.00 g polymethylphenyl siloxane, 0.40 g phenoxy ethanol, 0.20 g PHB-methylester, 8.00 g Momentive™ Cationic Emulsion®, 5.00 g isododecane, 0.40 g perfume oil, QSP water.

Leave-in Conditioner: 9.30 g xylose, 0.10 g vitamin E-acetate, 0.50 g polymethylphenyl siloxane, 10.00 g propylene glycol, 0.50 g behenyl trimethylammonium chloride, 0.05 g sodium chloride, 0.30 g d-panthenol, 0.30 g PHB-propylester, 2.00 g isododecane, 0.20 g perfume oil, QSP water.

Shampoo: 0.20 g Jaguar C-162, 40.00 g sodium laureth sulfate (LES 28%), 5.00 g Cocamidopropyl betaine, 2.00 g Dow Corning 200 Fluid/350 CS, 0.15 g perfume, 4.30 g xylose, 4.30 g arabinose, QSP water.

Further compositions disclosed in the European patent application 08151246.9 filed on 11 Feb. 2008 referenced as examples 2 to 7, 9 to 17, 19 to 21, 23, 24, 26 to 35, 37, 39 to 45, and 46—which are incorporated herewith by reference—are also suitable as a chassis for the composition according to the present invention.

The trade names/raw materials used in the examples are: Abilquat 3270 (Quaternium-80, 50% in propylene glycol) from Goldschmidt; Aculyn 48 (PEG-150/stearyl alcohol/SMDI copolymer, 19% in water) from Rohm and Haas; AMP 95% (aminomethylpropanol, 95% aqueous solution); Amphomer (octylacrylamide/acrylates/butylaminoethylmethacrylate copolymer); Aristoflex AVC (Ammonium Acryloyldimethyltaurate/VP copolymer); Aquaflex FX-64 (isobutylene/ethylmaleimide/hydroxyethylmaleimide copolymer, 40% strength in water/ethanol) from ISP; Aquaflex SF 40 (VP/vinyl caprolactam//DMAPA acrylates copolymer, 40% in ethanol) from ISP; Advantage S (vinyl caprolactam/VP/dimethylaminoethyl methacrylate copolymer); Carbomer-Carbopol (acrylic acid homopolmer); Celquat L200 (copolymer of hydroxyethylcellulose and diallyldimethylammonium chloride; Polyquaternium-4); GENAMIN CTAC 50 (cetrimonium chloride; cetyltrimethylammonium chloride); Copolymer 845 (VP/Ddimethylaminoethylmethacrylate copolymer, 20% in water) from ISP; Dehydol LS 4 (Lauryl alcohol tetraoxyethylen ether); Dekaben LMB (iodopropynyl butylcarbamate, 10% strength in butylene glycol); Dekaben LMP (Phenoxyethanol and iodopropynyl butylcarbamate); Diaformer Z-711 (acrylates/lauryl acrylate/stearyl acrylate/ethylamine oxide methacrylate copolymer, 40%) from Clariant; Dow Corning 1401 (High molecular weight Dimethiconol, 13% in cyclomethicone); Eumulgin L (PEG-1-PEG-9 lauryl glycol ether; Flexan (Sodium polystyrenesulfonate); GAFQUAT 755 N (Polyquaternium-11); Jaguar C-17/162 (guar hydroxylpropyltrimonium chloride) Laureth-4 (Lauryl alcohol tetraoxyethylen ether); Luviset Clear (Terpolymer of vinylpyrrolidone, methacrylamide and vinylimidazole) from BASF; Luviskol VA 64 (vinylpyrrolidone/vinylacetate copolymer); Luviskol K 90 Powder (vinylpyrrolidone); Luvimer 100 P (t-butyl acrylate/ethyl acrylate/methacrylic acid copolymer); Natrosol G (hydroxyethylcellulose); Pemulen (acrylates/C10-30 alkyl acrylate crosspolymer); Structure 3001 (acrylates/ceteth-20 itaconate copolymer, 30% strength in water) from National Starch; Surfactant 193 (Ethoxylated dimethylpolysiloxane) from Dow Corning); Synthalen W 2000 (acrylates/palmeth-25 acrylate copolymer, 31% in water); Tego Betain L 5045 (cocamidopropyl betaine).

PERFORMANCE DATA

Evaluation of Straightening Effect

As a measure for the evaluation of the straightening efficacy of a composition, it is possible to employ a hair shape scale that shows the change in shape of the hair after subsequent shampoo washing. If one starts with a curly strand of hair onto which a straight configuration has been impressed as a semi-permanent shape and onto which, is subsequently washed, the progression of the hair shape can be noted on a numbered scale.

Protocol for Preparation & Treatment

Shampooing: 0.4 ml of shampoo (Pantene® Clarifying Shampoo) is applied to 4 g, 10 inch naturally low lift hair. The shampoo is then gently massaged on hair with fingers for 30 sec.

Rinsing: Hair is thoroughly rinsed with water (at about 36° C.) using showerhead.

Drying: Hair is dried in a hot box at 140° F. (60° C.) for about 30 min.

Treatment: Split hair into 2 sections. Apply 0.5 ml composition according to the present invention to each section. Bring the sections together and apply the remaining product (0.5 ml).

Drying: Heat is applied on the hair using a blow dryer with brushing.

Shaping: Hair is shaped i.e. straightened using a flat iron at 450° F. (232° C.) with 8 passes.

Protocol: Performance Wash

Shampooing: 4 ml of shampoo (Hairtrition sulfate-free shampoo) is applied onto a hair switch. Hair is gently massaged with fingers for 1.5 min.

Rinsing: Hair is thoroughly rinsed with water (about 36° C.) by using showerhead for 2.5 min. Hair is then gently pressed together with the hands to drain off the water before wrapping the doll head into a towel and pressing to absorb water.

Combing: Hair is gently combed to mechanically refresh style.

Drying: Hair is blow-dried with diffuser (at about 45° C. for 10 min)

The performance wash may be repeated as often as needed.

Results

Evaluation of the Straightening Efficacy of the Reducing Sugar Comprising Composition:

Following the protocol detailed above, the hair switches are treated so that a semi-permanent style is created.

Following shampooing, the hair switches exhibit a change in style and noted on the scale. Specifically, hair without sugars shows less straightening (lower scale) than treated hair with various sugars.

TABLE 2

Straightening Efficacy After 1 and 10 washes

| Sugar | After Treatment | Straightening Efficacy after 1 performance wash | Straightening Efficacy after 10 performance washes |
|---|---|---|---|
| Control solution* | 10 | 3.3 | 3.3 |
| Ribose | 8.3 | 6.0 | 5.7 |
| Arabinose | 9.7 | 6.3 | 5.7 |
| Glucose | 9.7 | 5.0 | 4.7 |
| Fructose | 9.7 | 5.7 | 5.0 |
| Xylose | 8.3 | 5.3 | 4.3 |
| Sucrose | 10 | 4.3 | 4.0 |
| Methyl glucoside | 8.3 | 6.0 | 4.7 |

*Benedict's solution only.

Such data demonstrate the suitability of application of a reducing sugar comprising composition on hair for hair straightening.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair straightening method comprising:
(a) applying a hair care composition to hair, wherein the hair care composition comprises a reducing sugar from about 6% to about 20% by weight of the hair care composition, wherein the reducing sugar is selected from the group consisting of arabinose, ribose, and mixtures thereof; a buffering agent selected from the group consisting of glycine/sodium hydroxide, sodium carbonate/sodium hydrogen carbonate, sodium tetraborate/sodium hydroxide, sodium bicarbonate/sodium hydroxide, ammonium chloride/ammonia, and mixtures thereof and a cosmetically acceptable carrier;
(b) drying the hair;
(c) mechanically straightening the hair with a hair straightening appliance at a temperature of from about 100° C. to about 280° C.;
wherein the hair care composition is free of formaldehyde, methylene glycol, a ceramide compound, an alpha-hydroxy acid, thioglycolate, a thiolactate compound, a bisulfate compound, clay, a reducing agent, 1,3,5-trioxane, paraformaldehyde, a quaternary ammonium compound and a surfactant;

wherein the composition has a pH of from about pH 6 to about pH 10; wherein the method does not comprise a rinsing step between step (a) and step (c); and wherein the method does not use any coating material selected from a film coating material and sheet coating material.

2. The method of claim 1, wherein said reducing sugar is from about 12% to about 18% by weight of the hair care composition.

3. The method of claim 1, wherein the hair care composition comprises an antioxidant.

4. The method of claim 1, wherein the hair care composition comprises a conditioning agent, and wherein the conditioning agent is selected from the group consisting of epoxyaminosilane copolymers, polysiloxane/polyurea block copolymers, and mixtures thereof.

5. The method of claim 1, wherein the hair care composition has a pH of from about pH 6.5 to about pH 9.75.

6. The method of claim 1, wherein the hair care composition has a pH of from about pH 7.0 to about pH 9.5.

7. The method of claim 1, wherein the hair care composition has a pH of from about pH 8.0 to about pH 9.0.

* * * * *